United States Patent [19]
Daussin et al.

[11] Patent Number: 5,216,042
[45] Date of Patent: Jun. 1, 1993

[54] PROCESS FOR PREPARING VISCOSITY-STABILIZED REACTIVE TOLUENE DIISOCYANATE DISTILLATION RESIDUES AND BLENDS THEREOF

[75] Inventors: Rory D. Daussin, Bellaire; Steven B. Lowenkron, Houston; John L. Nafziger, Lake Jackson, all of Tex.

[73] Assignee: The Dow Chemical Company, Midland, Mich.

[21] Appl. No.: 727,707

[22] Filed: Jul. 10, 1991

[51] Int. Cl.$^5$ .............................................. C08G 18/00
[52] U.S. Cl. .................................. 521/160; 521/156; 521/170; 521/174; 528/76; 528/85; 568/767; 564/414
[58] Field of Search ............... 521/156, 160, 170, 174; 528/76, 85; 568/767; 564/414

[56] References Cited

U.S. PATENT DOCUMENTS

| | | |
|---|---|---|
| 2,680,127 | 6/1954 | Slocombe et al. |
| 2,822,373 | 2/1958 | Beck . |
| 3,140,305 | 7/1964 | Lowenstein . |
| 3,179,680 | 4/1965 | Kober . |
| 3,219,678 | 11/1965 | Kober et al. |
| 3,264,336 | 8/1966 | Powers . |
| 3,344,162 | 9/1967 | Rowton . |
| 3,362,979 | 1/1968 | Bentley . |
| 3,373,182 | 3/1968 | Powers . |
| 3,405,040 | 10/1968 | Ewald . |
| 3,452,073 | 6/1969 | Shultz . |
| 3,455,836 | 7/1969 | Shultz . |

(List continued on next page.)

FOREIGN PATENT DOCUMENTS 1458747 12/1976 United Kingdom .

OTHER PUBLICATIONS

CA 93:47803z.
CA 93:47804a.
CA 95:63438f.
CA 95:98778u.
CA 105:115886x.
CA 109:94157a.
CA 110:95975y.
Derwent 35349U-AE.
Derwent 55901S.
Derwent 68-84069P.
Derwent 89694P.
Derwent 90-059484.
Derwent 09365U-AE.
"Standard Test Method for Polyurethane Raw Materials: Determination of Hydrolyzable Chlorine of Isocyanates[1]", An American National Standard, 1987, pp. 565-566.
"Standard Test Method for Polyurethane Raw Materials: Determination of Acidity in Toluene Diisocyanate", An American National Standard, 1986, pp. 573-574.
Copending Application 07/727,707 (R. Johnson).

Primary Examiner—John Kight, III
Assistant Examiner—Duc Truong

[57] ABSTRACT

A method of preparing viscosity-stabilized toluene diisocyanate distillation residues comprising contacting toluene diisocyanate distillation residue with a material suitable for purging chloride-containing vapors under reaction conditions suitable to remove chloride-containing vapors from the toluene diisocyanate distillation residues. The material may be, for example, an aromatic solvent and/or a gas which associates, physically, chemically, or a combination thereof, with the vapors but not with significant amount of other components that may be present in the toluene diisocyanate distillation residue. The viscosity-stabilized and reactive residue can then be used alone or blended with one or more other isocyanate products, such as polymeric methylene diphenylisocyanate, to prepare materials such as polyurethane, polyisocyanurate, polyurethane-polyurea or polyurea compositions including, for example, foams.

13 Claims, No Drawings

U.S. PATENT DOCUMENTS

| | | |
|---|---|---|
| 3,457,291 | 7/1969 | Baylor . |
| 3,458,558 | 7/1969 | Cheng . |
| 3,516,950 | 6/1970 | Haggis ................... 521/160 |
| 3,549,504 | 12/1970 | Adica et al. . |
| 3,634,361 | 1/1972 | Shultz et al. .............. 521/160 |
| 3,781,320 | 12/1973 | Irwin . |
| 3,816,496 | 6/1974 | Schnabel . |
| 3,857,871 | 12/1974 | Hatfield, Jr. et al. . |
| 3,912,600 | 10/1975 | Hatfield, Jr. et al. . |
| 3,925,437 | 12/1975 | Renton ................... 521/162 |
| 4,076,577 | 2/1978 | Hetzel et al. . |
| 4,118,286 | 10/1978 | Burns et al. . |
| 4,118,586 | 10/1978 | Goldstein et al. ............ 568/767 |
| 4,137,266 | 1/1979 | Cassata ................... 564/414 |
| 4,138,424 | 2/1979 | Maekawa et al. . |
| 4,143,008 | 3/1979 | Zwolinski . |
| 4,193,932 | 3/1980 | Yamamoto et al. . |
| 4,251,401 | 2/1981 | Reischl . |
| 4,251,638 | 2/1981 | Reischl . |
| 4,293,456 | 10/1981 | Reischl . |
| 4,311,800 | 1/1982 | Reischl . |
| 4,465,638 | 8/1984 | Kan et al. . |
| 4,480,081 | 10/1984 | Rosin et al. . |
| 4,489,177 | 12/1984 | O'Conner et al. . |
| 4,506,044 | 3/1985 | Raes et al. . |
| 4,595,709 | 6/1986 | Reischl . |
| 4,604,410 | 8/1986 | Altenberg . |
| 4,774,357 | 9/1988 | Keggenhoff et al. . |
| 4,904,704 | 2/1990 | Nafziger et al. ............ 521/156 |

PROCESS FOR PREPARING VISCOSITY-STABILIZED REACTIVE TOLUENE DIISOCYANATE DISTILLATION RESIDUES AND BLENDS THEREOF

BACKGROUND OF THE INVENTION

This invention relates to distillation residues resulting from the preparation of toluene diisocyanate. More particularly, the invention relates to the preparation of viscosity-stabilized toluene diisocyanate distillation residues for use in the preparation of polyurethane and related products.

Toluene diisocyanates (hereinafter TDI) are commonly prepared by phosgenation of toluene diamines. Typical processes for the phosgenation of amines can be found in, for example, U.S. Pat. Nos. 2,680,127; 2,822,373; and 3,781,320. In the phosgenation of toluene diamines to prepare toluene diisocyanates the product diisocyanate is generally distilled from the reaction mixture in which it is prepared. At the conclusion of the distillation the reaction mixture normally contains a quantity of high boiling residue. Such residue generally comprises polymeric materials such as alpha, omega-isocyanatobiurets, polycarbodiimides, diisocyanato-carbodiimides, polyuretidinediones, isocyanurates and various other isocyanate adducts, such as hydrolyzable chlorides. This residue is typically discarded.

The disposal of this residue is a serious problem to the TDI industry. It is costly and poses safety problems. The handling of this material is a problem because special equipment is needed to move and store it prior to disposal.

Thus, it is desirable in the art to develop means of using these TDI distillation residues. A number of treatment methods have been developed, which include processes designed to convert the residues to entirely new materials, processes to use them as fillers in various plastics materials, and processes designed to "purify" them. For example, U.S. Pat. No. 4,506,040 discloses a process wherein TDI residue is reacted with an active hydrogen containing compound to form a polymer. The polymer is then dispersed in an organic solvent. A high molecular weight polyol is added and the solvent is removed, thereby producing a dispersion of the polymer in the high molecular weight polyol. The resulting dispersion is used to prepare polyurethane products, including foams and elastomers.

U.S. Pat. No. 4,480,081 discloses a process wherein a TDI distillation residue is reacted with a monohydroxylic compound, and the modified product is then reacted with a polyol. The final product is an isocyanate reactive compound for use in polyurethane formulations. U.S. Pat. No. 4,311,800 discloses a process wherein highly cross-linked insoluble distillation residues are reacted with water and then alcohol to form soluble compounds ontaining hydroxyalkyl and urethane groups. They may also be recyclized by simple hydrolysis into toluene diamines (TDA), which is the starting material from which TDI is derived. U.S. Pat. No. 4,489,177 discloses reaction of the TDI residue with a polyol to obtain a product having an OH-number of from 200 to 700. U.S. Pat. No. 3,455,836 discloses addition of 4,4'-methylene bis(phenylisocyanate) to liquid TDI distillation residue. The product can be reacted with active hydrogen containing materials.

German Patent 2,846,814 describes a process by which TDI bottoms are pulverized, treated with NCO-reactive compounds, and then dispersed in aliphatic polyols. The dispersions are used to manufacture urethane polymers. Another German Patent, 2,942,678, discloses mixing ground residues with certain monohydric alcohols, diols, or triols to produce a mixture containing at least 2 percent hydroxyl groups; heating the mixture at greater than 130° C. until homogeneous; and then cooling and grinding the product to use as a starting material in plastics. U.S. Pat. No. 4,595,709 shows preparation of polyaddition products containing urethane groups by reacting the TDI distillation residue with a compound containing hydroxyl groups such that the NCO/OH equivalent ratio is less than 1.5:1. The product can be used to prepare flame-resistant polyurethanes. U.S. Pat. No. 4,293,456 discloses use of the TDI residues directly as a reactive filler in polyurethanes to improve mechanical properties. U.S. Pat. No. 4,251,401 discloses producing suspension of the residues in polyhydroxyl compounds to use as the polyol component in forming polyurethanes. German Patent 2,846,815 discloses milling of the TDI residues, followed by treatment with isocyanate-reactive compounds to prepare reactive materials which are useful as fillers or dispersants.

None of the above methods allows use of the TDI distillation residues directly as the isocyanate component of a polyurethane formulation. In general TDI distillation residues are too acidic to be useful as such. Such acidity is often attributalbe, at least in part, to the presence of high levels of hydrolyzable chlorides, which respond as acids in standard analytical tests. The term "hydrolyzable chloride" as used herein refers to labile chlorine atoms which are ionically or covalently bonded within a compound, but are more reactive than, for example, the chlorine atom present in chlorobenzene. Hydrolyzable chloride concentration may also be referred to as chloride equivalent or chloride level. These hydrolyzable chlorides inhibit the reaction of the residues with active hydrogen compounds and therefore, when present in sufficient amount, may ultimately preclude use of the residues in preparing satisfactory polyurethane products.

Means to remove hydrolyzable chlorides include, for example, the process described in U.S. Pat. No. 4,904,704. That patent discloses a method in which the residues are reacted with at least about 0.5 equivalents, based on hydrolyzable chloride concentration in the residues, of an epoxy compound at an elevated temperature. The product has a hydrolyzable chloride concentration of less than about 800 parts per million. The resulting treated residue can be reacted, either alone or blended with other isocyanates, with an active hydrogen compound to form a polyurethane.

However, a problem encountered when TDI distillation residues, including those treated to reduce acidity and/or hydrolyzable chlorides, are used alone or blended with other polyisocyanates is that the products tend to be unstable over time with respect to viscosity. This presents problems in processing, and also a major obstacle to large-scale standardized production operations. Because of these problems those skilled in the art have avoided using TDI residues to prepare such polyurethanes.

It would be desirable in the art to find a process to prepare a toluene diisocyanate distillation residue that is relatively stable in viscosity and which also has a desirable reactivity when used to prepare a polyurethane product. By "viscosity stable" as used herein is meant that the residue increases in viscosity, if at all, more slowly than residues which have not received additional processing after their formation upon distillation from crude TDI.

SUMMARY OF THE INVENTION

Accordingly, the present invention provides, in one aspect, a method of preparing a viscosity-stable, reactive toluene diisocyanate distillation residue comprising contacting a toluene diisocyanate distillation residue with a material suitable for purging chloride-containing vapors under reaction conditions suitable to remove chloride-containing vapors. In preferred embodiments the material is an aromatic solvent, a gas, or a combination thereof.

In another aspect the present invention provides a method of preparing a viscosity-stable, reactive toluene diisocyanate distillation residue blend comprising blending (1) a tolune diisocyanate distillation residue prepared by contacting a toluene diisocyanate distillation residue with a material suitable for purging chloride-containing vapors under reaction conditions suitable to remove chloride-containing vapors, and (2) another isocyanate product.

In another aspect the present invention provides a viscosity-stable, reactive toluene diisocyanate distillation residue prepared by contacting a toluene diisocyanate distillation residue with a material suitable for purging chloride-containing vapors under reaction conditions suitable to remove chloride-containing vapors. In yet another aspect the present invention is a blend of (1) a viscosity-stable, reactive toluene diisocyanate distillation residue prepared by contacting a toluene diisocyanate distillation residue with a material suitable for purging chloride-containing vapors under reaction conditions suitable to remove chloride-containing vapors, and (2) another isocyanate product.

The present invention therefore provides compositions and methods of preparing treated toluene diisocyanate distillation residues to improve their viscosity stability and also reactivity, such that they can be successfully used, either alone or blended with one or more other isocyanate products, as the isocyanate component in a polyurethane formulation. In stabilizing viscosity the residues also exhibit an increased shelf life.

DESCRIPTION OF THE PREFERRED EMBODIMENTS

In the present invention the toluene diisocyanate distillation residues are preferably formed as a product of the phosgenation of toluene diamines. After phosgenation the product diisocyanate is removed from the reaction mixture by distillation. The distillation residue is that portion of the reaction mixture which remains following the removal of what has been conventionally considered as the toluene diisocyanate "product", i.e., that purified portion which has been conventionally sold to consumers. The residue is also frequently referred to as "TDI bottoms." The TDI residue to be employed herein preferably contains some amount of the pure toluene diisocyanate which has not been completely removed in the traditional distillation process, in an amount such that the distillation residue is generally a liquid at the temperatures at which it is produced, and more preferably also liquid at the temperature of the treatment of the present invention. The distillation residues referred to herein advantageously contain from about 13 to about 50, preferably from about 20 to about 30, weight percent free toluene diisocyanate. The distillation residues also preferably have an isocyanate group (NCO) content from 22 to about 45, preferably from about 25 to about 35, percent by weight and are substantially free of solvent used in their production.

If the distillation residue is released from the still immediately after separation of the purified toluene diisocyanate (i.e., the distillation overheads), it is generally a black tarry liquid. However, when a residue which is less than about 20 weight percent toluene diisocyanate is allowed to cool to about 35° C., the residue solidifies to a pitch-like solid which breaks upon impact but which flows over time. Such cooling delays irreversible hardening such as that typically observed within about 6 hours at about 150° C. to 250° C. Because the hardening occurs even at low temperatures, delays between production of the residue and its treatment as provided herein are preferably avoided. Optionally, the TDI bottoms can be dissolved in an organic solvent, such as an aromatic solvent including, for example, orthodichlorobenzene, monochlorobenzene, chlorobenzene, toluene, nitrobenzene, anisole, xylene, mixtures thereof, or the like shortly after their generation. Since the present invention includes heating the TDI bottoms in contact with a material suitable for purging or entraining chloride-containing vapors, dissolution of the TDI bottoms can be in such a material, e.g., in an organic solvent. This predissolution enables processing to complete implementation of the present invention to be delayed indefinitely, but preferably not more than three days following generation of the residues. In one embodiment of the present invention the formation of the bottoms and their dissolution in solvent are performed by one party, for example, a TDI manufacturer, and the final treatment of the bottoms to produce the product of the present invention is performed by another party, for example, a contractor.

The chemical composition of the bottoms is not certain, but they generally comprise a mixture of materials such as toluene diisocyanates, polyureas, (poly)biurets, alpha, omega-isocyanato-biurets, polycarbodiimides, polyuretidinediones, isocyanurates, diisocyanatocarbodiimides, addition products of monomeric diisocyanates and carbodiimides, polyisocyanates that have polyuretidinedione groups, phosgene and HCl adducts of carbodiimides and the like. Such materials usually contain free or capped isocyanate groups.

The distillation residues generally contain residual acidic materials. The term "acid" is used herein to refer to these contaminants and refers to free hydrogen chloride and/or labile covalently bonded chloride present in the isocyanate, such as carbamoyl chlorides and other various types of materials present in the isocyanate compounds that respond as acids in standard analytical tests. The acid content or level is readily determined by standard analytical tests such as ASTM D-4676 or other tests for acidity. These tests generally comprise heating the isocyanate in a solution of mixed alcohols or toluene and methanol, and titrating the resulting mixture with dilute potassium hydroxide. The acidity is expressed as weight percent hydrogen chloride, regardless of the actual identity of the acid-producing components.

The distillation residues also contain hydrolyzable chlorides, as defined hereinabove, which are present in the crude TDI stream and become more concentrated in the TDI bottoms. Hydrolyzable chloride can be determined separately from overall acid content by reacting the chloride in the isocyanates by hydrolysis or alcoholysis such as in a mixed alcohol solvent media, followed by titration of the resulting chloride ion concentration using silver nitrate or a similar compound.

Conveniently, to determine the hydrolyzable chloride content an admixture of a known weight of toluene diisocyanate distillation residue and a quantity of mixed alcohols, which boil preferably between about 50° C. and 150° C., more preferably between about 60° C. and about 125° C., and most preferably between about 80° C. and about 110° C., are reacted in amounts sufficient such that the products of the reaction remain in solution. Any mixture of alcohols which boils in that range and reacts with the residue to dissolve it is suitable. It is preferred that the alcohol mixture comprise an alkanol, such as methanol, and an alkanolether, such as methoxyethanol, methoxypropanol, or the like. A solution is formed by sufficiently stirring and heating the admixture, preferably to boiling, for a time sufficient to release the desired chlorides into solution. For the practice of the invention a time of from about 5 to about 10 minutes is preferred, more preferably from about 6 to about 8 minutes, and most preferably about 7 minutes.

Following heating, the solution is preferably removed from the heat and concentrated (85 percent by weight) nitric acid is added. It is preferred that the nitric acid be added in a quantity sufficient to make the solution acidic. This is preferably from about 0.5 to about 1 percent by weight of the total solution.

After the solution has cooled for a few minutes the electrodes are inserted and titration with a dilute solution of silver nitrate, e.g., 0.05 Normal (N), is begun. The titration is completed when an inflection point is reached. At this point the concentration of hydrolyzable chloride is calculated from the amount of silver nitrate required to reach the inflection point. In general, determination of chloride can be done according to, for example, the procedure of ASTM D-4663, using titration of chloride by silver nitrate and a carefully timed heating step prior to titration, as described hereinabove.

The hydrolyzable chloride concentration of a blend of the treated toluene diisocyanate residue product of the present invention and another isocyanate product is preferably less than about 800 parts per million (ppm), preferably less than about 600 ppm, more preferably less than about 400 ppm, and most preferably less than about 300 ppm. To prepare a blend diluents, such as low viscosity polyisocyanates including, for example, low viscosity diphenylmethanediisocyanate, derivatives thereof and related compounds, or aprotric coating-type solvents such as, for example, ethyl acetate and toluene, can be used.

In the practice of the present invention the TDI distillation residue starting material is heated in contact with a material which is suitable for purging chloride-containing vapors. This means that the material associates, either physically, chemically, or a combination thereof, with the chloride compounds present in the TDI bottoms, e.g., the hydrolyzable chloride compounds, but not with significant amounts of other components present in the TDI bottoms. Where there is a chemical reaction of the material with the chloride-containing vapors, such reaction is preferably reversible. Thus, the vapors are "purged" under specific reaction conditions. This purging allows separation of the material from the TDI bottoms and the resultant removal of the chloride-containing compounds.

One way to do this is to heat the TDI distillation residue dissolved in a solvent which is suitable for purging the chloride-containing vapors. As noted above, such dissolution preferably occurs soon after generation of the distillation residue. It is preferred that this solvent is an organic solvent in which the TDI distillation residue can be at least about 90 percent dissolved, and more preferably about 100 percent dissolved. The solvent can be selected from a wide range of organic and aromatic solvents, including but not limited to aromatic solvents such as orthodichlorobenzene (ODCB), chlorobenzene and other chlorinated solvents; toluene, nitrobenzene; anisole; xylene; mixtures thereof and the like. Other aprotic, preferably weakly nucleophilic solvents can also preferably be employed. It is preferred that the solvent be selected such that its boiling point is above about 40° C. at atmospheric pressure, more preferably from about 40° C. to about 260° C. at atmospheric pressure, and most preferably from about 150° C. to about 260° C.

The TDI residues/solvent solution is then heated to a temperature to distill it and thereby separate the solvent carrying the chloride-containing compounds from the bottoms, i.e., above the boiling point of the selected solvent. For example, in the case of using an aromatic chlorohydrocarbon such as orthodichlorobenzene (ODCB), the temperature is preferably from about 180° C. to about 200° C. The heating separates the solvent as a vapor and, if the TDI residues are going to be blended with another isocyanate product, is preferably continued until the TDI residues reach at least a 10 percent by weight concentration in the solvent, more preferably at least about 50 percent, and most preferably at least about 75 percent. If the TDI residues are not going to be blended with another isocyanate product, they are preferably distilled until they represent at least about 95 percent, more preferably at least about 99 percent, and most preferably at least about 99.9 percent by weight in the solvent.

Heating can be carried out either batch-wise or continuously, as a simple distillation or a partial or complete reflux, with or without fractionation. Removal of the solvent results in removal of significant amounts of hydrolyzable chlorides and resulting viscosity-stabilization. Solvent stripping can also be used to augment the removal of solvent, and can be effectively accomplished preferably at low pressure. For example, vacuum stripping can be employed to increase the amount of hydrolyzable chlorides removed from the bottoms.

In an alternative embodiment of the present invention the TDI bottoms are sparged with a gas which associates with the chloride-containing vapors but not significantly with other components of the TDI bottoms. Nitrogen or hydrogen chloride, for example, are preferred selections. This is preferably done with the bottoms dissolved in an organic solvent such as described hereinabove, and can be done before, during or after heating in contact with a material suitable for purging or entraining the chloride containing vapors. It is to be understood that this is treatment of the TDI bottoms only, and not treatment of the crude TDI stream prior to the conventional distillation which separates a "purified" commercial TDI product from the TDI distillation residue. For example, when orthodichlorobenzene is selected, it is preferred that the heating takes place in a range of from about 50° C. to about 230° C., more preferably from about 140° C. to about 220° C., and most preferably from about 160° C. to about 200° C.

Total time can vary preferably from about 5 minutes to about 210 minutes. At the most preferred temperature range the residence time is preferably from about 1 to about 3 hours. Those skilled in the art will know to balance temperature and residence time to achieve acceptable or desirable processing economics and to optimize chloride reduction within the range of the selected processing condition ranges.

Following the treatment by distillation and solvent removal with or without a gas, e.g., nitrogen, sparge, the treated TDI distillation residues of the present invention are preferably sufficiently viscosity-stabilized and concentrated to allow blending with another isocyanate product if such is desired. Blending allows for a cost saving as compared with using 100 percent of the more expensive and more commonly used isocyanate products, such as methane diphenyldiisocyanate (MDI) or polymethylene polyphenylisocyanates such as polymeric methylene diphenylisocyanates (PMDI), in preparing a polyurethane product. It also enables viscosity control and allows for adjustment, generally increases, in reactivity, as evidenced by foam formation and the qualities of the foam formed.

For the purposes of this invention, the term "reactive" is defined as the ability of the TDI bottoms to react with a compound containing an active hydrogen containing group. Any suitable organic compound containing an active hydrogen containing group, as determined by the Zerewitinoff method, may be used for reaction with the treated distillation bottoms of the present invention or blends thereof with other polyisocyanates. Active hydrogen compounds are compounds having hydrogen-containing functional groups which will react with an isocyanate group. The Zerewitinoff test described by Kohler in the *Journal of the American Chemical Society*, Vol. 49, page 3181 (1927) predicts the tendency of a hydrogen-containing group to react with isocyanates.

It is not critical to the present invention at what point in the process other isocyanate products or compounds is/are added to the treated TDI bottoms: Before, during or after treatment are each suitable points at which to perform the blending. Blending with the polyisocyanate compound after the treatment of this invention is generally preferred to avoiding reaction of the polyisocyanate compound with minor species that may be present in the untreated TDI residues. Some blending before treatment may be nonetheless desirable, however, particularly in situations where the untreated residue is inconveniently viscous. The polyisocyanate used for dilution prior to treatment is suitably any, preferably liquid, organic isocyanate compound having an average of more than one isocyanate group per molecule. The polyisocyanate compounds are well known and are readily available commercially.

Exemplary suitable polyisocyanates include aromatic, aliphatic and cycloaliphatic polyisocyanates and combinations thereof. Representative polyisocyanates include diisocyanates such as m-phenylene diisocyanate, toluene-2,4-diisocyanate, toluene-2,6-diisocyanate, hexamethylene-diisocyanate, tetramethylene-diisocyanate, cyclohexane-1,4-diisocyanate, hexahydrotoluene diisocyanate (and isomers thereof), 1-methoxyphenyl-2,4-diisocyanate, diphenylmethane-4,4'-diisocyanate, diphenylmethane-2,4; -diisocyanate, 3,3'-dimethyl-4,4'-biphenyl diisocyanate, 3,3'-dimethyldiphenyl-methane-4,4'-diisocyanate and the like; triisocyanates such as 4,4',4"-triphenylmethane triisocyanate, toluene-2,4,6-triisocyanate, and the like; tetraisocyanates such as 4,4'-dimethyldiphenyl-methane2,2',5,5'-tetraisocyanate, 4,4'-dimethyldiphenyl-methane2,2',5,5'-tetraisocyanate, 4,4'-dicyclohexane-diisocyanate, isophorone diisocyanate, isomers of each and the like; as well as other polyisocyanates such as polyphenylisocyanate and the like and mixtures thereof. Toluene diisocyanate, diphenylmethane-4,4'-diisocyanate, diphenylmethane-2,4'-diisocyanate and polymethylene polyphenylisocyanate are beneficial for use in the practice of the invention because of their availability and properties. Mixtures of two or more of these polyisocyanates with the treated TDI bottoms of the present invention are also suitably used.

Polymethylene polyphenylisocyanates, toluene diisocyanates and polymeric methylene diphenylisocyanates (PMDI) are preferred for use in the practice of the invention. Polymethylene polyphenylisocyanates are mixtures containing preferably from about 35 to about 85 percent by weight, more preferably from about 65 to about 75 percent by weight, of methylenebis(phenylisocyanate), the remainder of the mixture being closely related polyisocyanates of higher molecular weight and functionality greater than about 2. They are well-known compositions, and are commercially prepared by phosgenation of mixtures of the corresponding methylene-bridged polyphenyl polyamines. The latter are, in turn, obtained by interaction of formaldehyde, hydrochloric acid and primary aromatic amines such as aniline, o-chloroaniline, o-toluidine, and the like, using procedures well known in the art. Illustrative of known methods for preparing methylene-bridged polyphenyl polyamines and polymethylene polyphenylisocyanates therefrom are those described in U.S. Pat. Nos. 2,683,730; 2,950,263; 3,012,008; 3,344,162; and 3,362,979; Canadian Patent No. 700,026; and German Patent Application 1,131,877. Polyisocyanates suitable for use in the practice of the invention include those commercially available from the Dow Chemical Company under the trade designation PAPI*.

The blends preferably comprise from about 1 to about 99 percent by weight of the treated TDI bottoms and from about 99 to about 1 percent of the polyisocyanate. Proportions of treated TDI bottoms to be blended with another selected polyisocyanate are preferably calculated to produce a resultant isocyanate having a preselected desired viscosity, as well as preselected properties in polyurethane products prepared therefrom. Because the treated TDI bottoms are generally of a higher viscosity than that of the polyisocyanate, the polyisocyanate can be referred to herein as the "diluent." The final blend viscosity is preferably less than about 10,000 centipoise (cps), more preferably less than about 3,000 cps, and most preferably from about 40 to about 2,500 cps. When a blend is to be used for a specific application, the viscosity is most preferably preselected for convenience in preparing that type of foam by processes known to those skilled in the art. For instance, in the case of insulative rigid polyurethane foams, viscosity is generally preferably from about 40 to about 2,000 cps.

When polymethylene polyphenylisocyanates are blended with the treated toluene diisocyanate residues, blends are preferably at least as reactive as the starting polymethylene polyphenylisocyanates. This reactivity is measured by the times from mixing of isocyanates with active hydrogen compounds until specific phenomena are observed in a forming polyurethane or polyisocyanurate foam. These measures of reactivity conventionally include cream time, visual rise time, gel time, and tack-free time.

In preparing treated TDI bottoms, either for use alone or as a component of a treated TDI bottoms/polyisocyanate blend as described, it is desirable, as already noted, that all solvent used in the treatment of the present invention be removed prior to reaction to prepare a polyurethane. Preferably, as noted above, the solvent is removed by heating the TDI bottoms or TDI bottoms/polyisocyanate blend using low pressure methods known to those skilled in the art, e.g., vacuum stripping. If necessary, however, a second distillation can be performed following blending to remove any remaining solvent. There is preferably no more than trace amounts of solvent present in the final, viscosity-stabilized product, preferably less than about 1 percent by weight, more preferably less than about 0.008 percent by weight. This can be determined by means of standard gas chromatography using methods known to and conventionally used by those skilled in the art.

Following removal of the solvent the treated TDI residues or treated TDI residues/polyisocyanate blend product is preferably cooled. This cooling is preferably done to about 50° C. over a very short time period, preferably in less than about 60 minutes, more preferably less than about 30 minutes, and most preferably less than about 5 minutes. The product is then preferably stored at about 50° C. for from 1 to 14 days, more preferably about 7 days, and then allowed to cool to 25° C. This allows reequilibrium of the viscosity-affecting materials. A cooling step can also be done if desired. Following preparation of the treated TDI bottoms product it is ready for use in preparing a final product, such as a polyurethane, polyurea, or polyisocyanurate product or a prepolymer useful to prepare a final product, by reacting it with an active hydrogen compound.

The viscosity-stabilized toluene diisocyanate distillation residues and blends thereof with liquid polyisocyanates are suitably used to make liquid polyisocyanurates, polyurethanes, polyurethane-polyurea and polyurea polymers and the like. Rigid polyisocyanurate and polyurethane foams prepared using the blends of the invention are particularly useful because of their low K factors. Polyisocyanurate foams (also called "isocyanurate foams") are foams formed using a ratio of isocyanate groups to active hydrogen groups of preferably at least about 1.3, in the presence of trimerization catalysts as discussed hereinafter. Polyurethane foams are formed when only a small amount of trimerization of the isocyanate takes place, and polymer formation is primarily the reaction of active hydrogen groups of an active hydrogen component with isocyanate groups of a polyisocyanate component.

Rigid foams are foams which rupture when a 200×25×25 millimeter sample is bent around a 25 millimeter mandrel at a uniform rate of one lap in 5 seconds at a temperature between about 18° C. and 29° C., according to ASTM 1566-82. Flexible foams do not generally rupture under these conditions. Advantageously, a rigid foam prepared using the viscosity-stabilized TDI residues or blends thereof of the present invention has a tensile strength to compressive strength ratio of about 1:0.5.

Any suitable organic compound containing at least one active hydrogen-containing group, preferably two or more, as determined by the Zerewitinoff method, can be used for reaction with the stabilized distillation residues or blends thereof. Active hydrogen compounds are compounds having hydrogen-containing functional groups which will react with an isocyanate group. The Zerewitinoff test described by Kohler in the *Journal of the American Chemical Society*, Vol. 49, (1927) 3181, predicts the tendency of a hydrogen-containing group to react with isocyanates. Suitable active hydrogen compounds are those conventionally employed in the preparation of polyurethanes, such as the compounds described in U.S. Pat. No. 4,394,491, and also polyureas. This patent terms the active hydrogen compounds "polyahls." Suitable active hydrogen compounds are generally liquids or solids capable of being melted at relatively low temperatures.

Active hydrogen components most commonly used in polyurethane production are those compounds having at least 2 hydroxyl groups, which compounds are referred to as "polyols." Representatives of suitable polyols are generally known and are described in such publications as Saunders et al., "Polyurethanes, Chemistry and Technology," *High Polymers*, Vol. Interscience Publishers, New York, Vol. 1 and XVI (1962) 32–42 and 44–45, and Vol. 5–6 (1964) 198–199; *Kunstoff-Handbuch*, Vieweg-Hochtlen, Carl Hanser-Verlag, Munich, Vol. 7 (1966) 45–71; Saunders, *Organic Polymer Chemistry*, Chapman and Hall, London (1973) 323–325; and *Developments in Polyurethanes*, J. M. Burst, ed., Applied Science Publishers, Vol. 1 (1978) 1–76.

Typical polyols include polyester polyols, polyester amide polyols, and polyether polyols having at least 2 hydroxyl groups. Polyethers and polyesters having hydroxyl terminated chains are preferred for use as relatively high molecular weight active hydrogen-containing compounds for use in polyurethanes suitable for use in the practice of the invention. Examples of polyols also include hydroxy functional acrylic polymers, hydroxyl-containing epoxy resins, polyhydroxy terminated polyurethane polymers, polyhydroxyl-containing phosphorus compounds and alkylene oxide adducts of polyhydric thioethers, including polythioethers and acetals, such as polyacetals.

Polyether polyols advantageously employed in the practice of this invention are polyalkylene polyether polyols including the polymerization products of oxiranes or other oxygen-containing heterocyclic compounds such as tetramethylene oxide in the presence of such catalysts as boron trifluoride potassium hydroxide, triethylamine, tributyl amine and the like, or initiated by water, polyhydric alcohols having from about 2 to about 8 hydroxyl groups, amines and the like. Illustrative alcohols suitable for initiating formation of a polyalkylene polyether include ethylene glycol, 1,3-propylene glycol, 1,2-propylene glycol, 1,4-butylene glycol, 1,3-butylene glycol, 1,2-butylene glycol, 1,5-pentane diol, 1,7-heptane diol, glycerol, 1,1,1-trimethylolpropane, 1,1,1-trimethylolethane, hexane-1,2,6-triol, alpha-methyl glucoside, pentaerythritol, erythritol, pentatols and hexatols. Sugars such as glucose, sucrose, fructose, maltose and the like as well as compounds derived from phenols such as (4,4'-hydroxyphenyl)2,2-propane, and the like are also suitable polyhydric alcohols for forming polyether polyols useful in the practice of the invention.

The treated distillation residues of the invention are advantageously reacted with active hydrogen compounds in the presence of blowing agents. Any blowing agent or mixture thereof is suitable for use in the practice of the invention. Suitable blowing agents include inorganic blowing agents such as water, organic blowing agents which are volatile at temperatures in the mold, and dissolved inert gases. Suitable organic blowing agents include acetone; ethyl acetate; methanol; ethanol; halogen-substituted alkanes such as methylene chloride, chloroform, ethylidene chloride, vinylidene chloride, monofluorotrichloromethane, chlorodifluoromethane, dichlorodifluoromethane and the like; butane; hexane; heptane; diethyl ether; and the like. Gases inert to the starting componenes such as nitrogen, air, carbon dioxide and the like are also useful blowing agents. Compounds such as azides which decompose at temperatures present in the mold to produce gases such as nitrogen are also useful. Preferred blowing agents are compounds which boil from about $-50°$ C. to about $100°$ C., more preferably from about $0°$ C. to about $50°$ C.

The amount of such blowing agent employed is not critical to the invention, but should be sufficient to foam the reaction mixture. This amount will vary with factors such as the density desired in a foamed product.

Water is another useful blowing agent for use in the practice of the invention. In addition to generating carbon dioxide for foaming, water reacts quickly with polyisocyanate components, thus contributing to early polymer strength needed for gas retention. Generally, when water is used it is present in proportions of from about 1.5 to about 8 weight percent of water, based on total weight of active hydrogen components. Other blowing agents, such as those previously discussed, can be used with water.

Rigid polyisocyanurate and polyurethane foams prepared from the viscosity-stabilized distillation residues and blends of the invention are particularly useful. Those skilled in the art of preparing such foams can readily use the treated TDI distillation residues and blends thereof with additional polyisocyanates to prepare polyurethanes and related products. For instance, the process of U.S. Pat. No. 4,604,410 can be followed, substituting the treated TDI bottoms or blends of the invention for other polyisocyanates. Preferably, the compositions of the invention are reacted with a polyfunctional active hydrogen compound in the presence of a catalyst, which catalyzes the formation of isocyanurates, and a blowing agent suitable for forming foams having preselected physical properties.

Suitable catalysts are any which catalyze the formation of isocyanurates such as those mentioned in *High Polymers*, Vol. 16, "Polyurethanes, Chemistry and Technology" by Saunders and Frisch, Interscience Publishers, New York, part 1 (1962) 94–97. Such catalysts are referred to herein as trimerization catalysts. Exemplary of these catalysts include aliphatic and aromatic tertiary amine compounds, organometallic compounds, alkali metal salts of carboxylic acids, phenols and symmetrical triazine derivatives. Preferred catalysts include potassium salts of carboxylic acids such as potassium octoate and tertiary amines such as, for instance, 2,4,6-tris(dimethyl aminomethyl) phenol.

Preferred active hydrogen compounds for use in preparing rigid isocyanurate foams are those having equivalent weights less than about 240, more preferably less than about 200. Among those active hydrogen compounds, polyester polyols, such as those prepared from terephthalic acid and polyalkylene glycols such as polyethylene glycols, are generally preferred over the polyether polyols. The treated TDI bottoms alone or in blends with one or more additional polyisocyanates are advantageously reacted with the polyfunctional active hydrogen compounds in a ratio of from about 1.3 to about 6, preferably about 2 to about 4, equivalents of isocyanate to active hydrogen groups, to form foams high in isocyanurate groups.

In the preparation of isocyanurate foams, the blowing agent is most preferably at least partially a hydrocarbon or halohydrocarbon. The blowing agent is advantageously used in an amount sufficient to achieve a preselected density between about 0.4 and 20 pounds per cubic foot (pcf), preferably from about 1 to about 5 pcf. Such densities are advantageously achieved using from about 1 to about 30 percent by weight blowing agent based on total formulation weight (including all active hydrogen compounds, polyisocyanates and additives).

For example, rigid polyisocyanurate foams of the invention preferably have K factors which are lower than corresponding foams manufactured from polymethylene polyphenylisocyanates of the same viscosities, using identical active hydrogen compounds, blowing agents, catalysts, surfactants and other additives by at least about 0.003 BTU in./hr.-ft$^2 \times °$F. Preferably such foams have K factors lower than corresponding foams by at least about 3 percent, more preferably at least about 5 percent. More preferably, the foams of the present invention have K factors (mean temperature at $75°$ F.) of less than about 0.115, preferably less than about 0.112, more preferably from about 0.102 to about 0.112 BTU in./hr.-ft$^2 \times °$F. Rigid isocyanurate foams of the invention also advantageously have less tendency to crumble, as determined by the friability test described in ASTM C-421-77, than foams prepared from polymeric methylene diphenylisocyanate of the same viscosity used in otherwise similar formulations. The percent friability of foams of the invention is advantageously less than about 60 percent, more preferably less than about 50 percent, and most preferably less than about 40 percent of that of a corresponding foam prepared using polymeric methylene diphenylisocyanate.

Any effective method conventionally known to and used by those skilled in the art can effectively be used to prepare a polyurethane, polyurea/polyurethane, or polyisocyanurate foam of the present invention. The treated TDI bottoms or blends thereof are simply substituted for other polyisocyanates in applicable formulations. Preferably, the residues or blends of the present invention are reacted with a polyfunctional active hydrogen compound in the presence of a catalyst which catalyzes the formation of polyurethane bonds and a blowing agent suitable for forming foams having preselected physical properties.

One or more catalysts are beneficially used in making polyurethanes. Suitable catalysts for preparation of polyurethane foams are any which catalyze reactions of isocyanates with active hydrogen groups such as hydroxyl groups or catalyze the reaction between water and an isocyanate such as those mentioned in Saunders et al., "Polyurethanes, Chemistry and Technology", *High Polymers*, Interscience Publishers, New York, Vol. XVI, part 1 (1962) 211–215. Such catalysts are referred to herein as polyurethane catalysts. Suitable catalysts include tertiary amines, such as, for example, triethylenediamine, N-methyl morpholine, N-ethyl morpholine, diethyl ethanolamine, 1-methyl-4-dimethylaminoethyl piperazine, 3-ethoxy-N-dimethylpropylamine, N,N-dimethyl-N',N'-methyl isopropyl propylene diamine, N,N-diethyl-3-diethylaminopropylamine, dimethyl benzylamine, triethylamine, tributylamine, bis(N,N-diethylamino-ethyl)adipate, 2-methylimidazole, 1,4-diaza-bicyclo-(2,2,2)-octane and the like. Other suitable catalysts include tin compounds such as stannous chloride, tin salts of carboxylic acids such as dibutyltin di-2-ethyl hexoate, dibutyl tin dilaurate, dibutyltin diacetate, di-2-ethylhexyltin oxide, stannous octoate and the like, as well as other organometallic compounds such as compounds of iron, lead, arsenic, antimony, mercury and bismuth and compounds disclosed in U.S. Pat. No. 2,846,408 and the like. Silamines having carbon-silicon bonds such as those described in German Patent 1,229,290 including 2,2,4-trimethyl-2-silamorpholine and the like as well as basic nitrogen compounds such as tetraalkylammonium hydroxides, alkali metal hydroxides such as sodium hydroxide, alkali metal phenolates such as sodium phenolate, and alkali metal alcoholates, such as sodium methylate, hexahydrotriazines and the like are also useful catalysts.

Mixtures of catalysts are generally beneficial when water is used in the polyurethane-forming formulations. Tertiary amines are effective in catalyzing reaction between water and isocyanate groups. Transition metal salts and complexes are effective in catalyzing polymerization of polyisocyanates and other active hydrogen components, like polyols. Mixtures of such transition metal compounds as compounds of tin, iron and the like with tertiary amine catalysts are, therefore, preferably used in the practice of the invention.

Metal atom-containing catalysts are generally used in a quantity of from about 0.0025 to 0.5 percent by weight based on active hydrogen containing starting components. Amine catalysts are generally used in a quantity of from about 0.001 to 5 percent by weight based on active hydrogen containing starting components. Those skilled in the art are able to select a catalyst composition and quatity suitable to accelerate the reaction between starting components. Representative catalysts and details regarding their use are found in *Kunstoff-Handbuch*, Vieweg and Hochtlen, Carl Hanser-Verlag, Munich, Vol. VII (1966) 96–102.

Active hydrogen compounds suitable for forming the isocyanurate foams are also suitable for forming the polyurethane foams. However, in the case of rigid polyurethane foams, the preferred polyols are polyether polyols, polyester polyols and blends thereof. The polyether polyols are preferably those initiated by sucrose, glycerine, toluene diamine, aminoethylpiperazine and the like and mixtures thereof. Among such preferred polyether polyols are polyalkylene oxide polymers such as polymers of ethylene oxide, propylene oxide, butylene oxide and the like. The polyols or blends thereof advantageously have equivalent weights of from about 120 to about 230, preferably from about 125 to about 135. Polyols or other active hydrogen compounds are preferably reacted with the polyisocyanate blends containing the viscosity-stabilized TDI residues in amounts sufficient to achieve an isocyanate index suitably from about 60 to about 150, preferably from about 90 to about 125, more preferably from about 100 to about 120. The isocyanate index is the ratio of isocyanate groups to active hydrogen groups times 100.

Blowing agents suitable for use in forming polyisocyanurate foams are also suitable for forming polyurethane foams. Preferred blowing agents include carbon dioxide, trichlorofluoromethane, 1,1-dichloro2,2,2-trifluoroethane, 1,1-dichloro-1-fluoroethane. The amount of such blowing agent employed is not critical to the invention, but should be sufficient to foam the reaction mixture. Said amount will vary with factors such as the density desired in a foamed product. The density of a rigid polyurethane foam of the invention is advantageously preselected between about 1.90 and 2.27 pounds per cubic foot (pcf), preferably from about 1.90 to about 2.05 pcf. Such densities are advantageously achieved using from about 13 to about 14 percent by weight blowing agent in the absence of any water based on total formulation weight (including all active hydrogen compounds, polyisocyanates and additives). Water is also useful as a blowing agent for use in forming the polyurethane foams. Generally, when water is used, it is present in proportions of from about 0.5 to about 3.5 weight percent of water based on total weight of active hydrogen components. Mixtures of blowing agents are also suitably used.

For example, rigid polyurethane foams of the invention preferably have K factors (mean temperature at 75° F.) of less than about 0.125, more preferably less than about 0.120 BTU×in./hr.-ft.$^2$×°F. As is known to those skilled in the art, the K factor is determined by a number of variables, including, for example, the selection of active hydrogen compound.

Additives such as surface active agents, antistatic agents, plasticizers, fillers, flame retardants, pigments, stabilizers such as antioxidants, fungistatic and bacteriostatic substances and the like are optionally used in foams of the invention. Selection and use of such compounds is within the skill in the art.

In producing foams by the processes of the invention, it is often advantageous use a foam stabilizer, catalyst and blowing agent in balanced proportions to obtain a foam of a preselected cell size, structure and density. Suitable foam stabilizers are generally wetting agents or surface active agents. Nonionic surfactants and wetting agents are generally preferred. Suitable foam stabilizers include hydrophilic, and advantageously water soluble, organo-silicon compounds, such as those having a polydimethylsiloxane group attached to a copolymer of ethylene oxide and propylene oxide and the like. Exemplary foam stabilizing compounds are disclosed in U.S. Pat. No. 2,764,565. Such foam stabilizers, surface active compounds and proprietary combinations thereof are generally commercially available with specific instructions as to their use.

The following examples are offered only for purposes of illustrating the process of the present invention and are not to be viewed as limitative of its scope. All parts and percentages are on a weight basis unless otherwise indicated.

EXAMPLE 1

About 82.0 g of TDI distillation residue resulting from commercial preparation of TDI, containing about 4,000 ppm chloride, is dissolved in about 394.5 g of orthodichlorobenzene (ODCB). This 80 percent ODCB/20 percent TDI bottoms solution is heated to distill it with concurrent solvent removal at about 190° C. The distillation is stopped when the ODCB concentration is about 20 percent. Polymeric methylenediphenylisocyanate (PMDI) having a viscosity of about 42 centipoise (cps) is blended with the treated TDI bottoms/ODCB solution. The blend is prepared such that the final treated TDI bottoms/PMDI blend product is composed of about 25 percent treated TDI bottoms and 75 percent PMDI. In order to remove the remaining solvent, the resultant mixture is heated at about 150° C. and about 8 mm Hg pressure.

After 30 minutes of solvent removal, the treated TDI bottoms/PMDI mixture is allowed to cool to about 50° C. This treated TDI bottoms/PMDI blend product is stored at about 50° C. for 3 days to allow reequilibration of viscosity, and then allowed to cool to about 25° C. The blended product has a hydrolyzable chloride level of about 237 ppm chloride. A urethane reactivity test gives a relative cream time of 45 seconds. The viscosity growth rate is as shown in Table 1.

TABLE 1

| TIME (Days) | VISCOSITY (at 25° C.) | INSTANTANEOUS VISCOSITY GROWTH RATE at 25° C. (% Per Month) | VISCOSITY (at 50° C.) | INSTANTANEOUS VISCOSITY GROWTH RATE at 50° C. (% Per Month) |
|---|---|---|---|---|
| 0 | 304 | n/a | 304 | n/a |
| 14 | 332 | 19.7 | 379 | 52.9 |
| 28 | 329 | −1.9 | 414 | 19.8 |
| 42 | 344 | 9.8 | 438 | 12.4 |
| 56 | 351 | 4.4 | 480 | 20.5 |
| 90 | 365 | 3.5 | 573 | 17.1 |
| 119 | 376 | 3.1 | 699 | 22.7 |
| 154 | 377 | 0.2 | 785 | 10.5 | n/a indicates not applicable, i.e., row shows only starting viscosities after reequilibration (at 3 days after mixing).

EXAMPLE 2

TDI bottoms (121.0 g) is admixed with 362.4 g of PMDI. The viscosity of the PMDI is about 40 centipoise (cps). The resultant mixture has a viscosity of about 160 cps. The blend is poured into a 1,000-mL, round-bottom flask equipped with a nitrogen sparger, magnetic stirrer, heating mantle and stirrer. Nitrogen is then sparged though the blend at about 350 mL/min. and the mixture is heated.

After about 20 minutes, a temperature of about 170° C. is attained and held for about 3 hours. The blend is quickly cooled by immersion of the flask into an icewater bath. Acidity is measured at 147 ppm. Aliquots of the treated TDI bottoms:PMDI blend are placed in 4-dram vials, sealed and stored at 25° C. and 50° C. The solutions are allowed to reequilibrate for 3 days before viscosity measurements are taken. Viscosity measurements are shown in Table 2.

TABLE 2

| TIME (Days) | VISCOSITY (at 25° C.) | INSTANTANEOUS VISCOSITY GROWTH RATE at 25° C. (% Per Month) | VISCOSITY (at 50° C.) | INSTANTANEOUS VISCOSITY GROWTH RATE at 50° C. (% Per Month) |
|---|---|---|---|---|
| 0 | 309 | n/a | 309 | n/a |
| 14 | 327 | 12.5 | 352 | 29.8 |
| 28 | 338 | 7.2 | 395 | 26.2 |
| 49 | 343 | 2.1 | 449 | 19.5 |
| 83 | 355 | 3.1 | 582 | 26.1 |
| 121 | 359 | 0.9 | 804 | 30.1 |
| 162 | 371 | 2.4 | 1278 | 43.1 |
| 191 | 380 | 2.5 | — | — | n/a indicates not applicable, i.e., row shows only starting viscosities after reequilibration (at 3 days after mixing).
— denotes no data available.

EXAMPLE 3

A treated TDI bottoms/PMDI blend is prepared using the method and amounts of Example 1, except that the final solvent removal step is done prior to blending of the treated TDI bottoms and PMDI, rather than after the blending as in Example 1.

COMPARATIVE EXAMPLE

About 96.8 g of untreated TDI bottoms is blended with about 290.1 g of PMDI having a viscosity of about 42 cps. The hydrolyzable chloride level is calculated as about 1,157 ppm chloride. The urethane reactivity test gives a relative gel time of about 53 seconds. The viscosity growth rate is as shown in Table 3.

TABLE 3

| TIME (Days) | VISCOSITY (at 25° C.) | INSTANTANEOUS VISCOSITY GROWTH RATE at 25° C. (% Per Month) | VISCOSITY (at 50° C.) | INSTANTANEOUS VISCOSITY GROWTH RATE at 50° C. (% Per Month) |
|---|---|---|---|---|
| 0 | 278 | n/a | 278 | n/a |
| 14 | 313 | 27.0 | 609 | 255.1 |
| 28 | 331 | 12.3 | 1882 | 447.9 |
| 42 | 351 | 12.9 | 4608 | 310.4 |
| 56 | 367 | 9.8 | 18169 | 630.6 |
| 90 | — | — | — | — |
| 119 | 442 | 9.7 | — | — |
| 154 | 519 | 14.9 | — | — | n/a indicates not applicable, i.e., row shows only starting viscosities after reequilibration (at 3 days after mixing).
— denotes no data available.

What is claimed is:

1. A method of preparing a viscosity-stable reactive toluene diisocyanate distillation residue comprising contacting the toluene diisocyanate distillation residue with a solvent, gas or mixture thereof suitable to purge chloride-containing vapors under reaction conditions suitable to remove chloride containing vapors from the toluene diisocyanate distillation residue.

2. The method of claim 1 wherein the solvent is an aromatic solvent selected from orthodichlorobenzene, toluene, benzene, nitrobenzene, anisole, xylene, monochlorobenzene, and mixtures thereof.

3. The method of claim 1 further comprising blending the viscosity-stabilized toluene diisocyanate distillation residue with another isocyanate product.

4. The method of claim 3 wherein the other isocyanate product is polymeric methylene diphenylisocyanate, toluene diisocyanate, or a mixture thereof.

5. The method of claim 1 wherein the contacting is done at a temperature from about 150° C. to about 230° C.

6. The method of claim 5 wherein the contacting is done at a temperature from about 190° C. to about 210° C.

7. The method of claim 1 wherein the contacting is done for a time period from about 5 to about 210 minutes.

8. The method of claim 1 wherein the gas is nitrogen.

9. A viscosity-stable reactive toluene diisocyanate distillation residue composition prepared by the method of claim 1.

10. A method of preparing an isocyanate blend compositiong comprising blending (1) a viscosity-stable, reactive toluene diisocyanate distillation residue prepared by the method of claim 1, and (2) another isocyanate product.

11. An isocyanate blend composition comprising (1) a viscosity-stable, reactive toluene diisocyanate distillation residue prepared by the method of claim 1, and (2) another isocyanate product.

12. A polyurethane, polyurea, polyurethanepolyurea or polyisocyanurate composition prepared from a formulation comprising a viscosity-stable, reactive toluene diisocyanate distillation residue prepared by the method of claim 1.

13. The composition of claim 12 wherein the composition is a rigid foam.

* * * * *